US009320908B2

(12) United States Patent
Fletcher et al.

(10) Patent No.: US 9,320,908 B2
(45) Date of Patent: Apr. 26, 2016

(54) APPROVAL PER USE IMPLANTED NEUROSTIMULATOR

(75) Inventors: Kellie S. Fletcher, San Francisco, CA (US); Benjamin David Pless, Atherton, CA (US); Anthony Caparso, San Jose, CA (US); Kenneth N. Horne, San Francisco, CA (US)

(73) Assignee: Autonomic Technologies, Inc., Redwood City, CA (US)

( * ) Notice: Subject to any disclaimer, the term of this patent is extended or adjusted under 35 U.S.C. 154(b) by 823 days.

(21) Appl. No.: 12/688,524

(22) Filed: Jan. 15, 2010

(65) Prior Publication Data
US 2010/0179617 A1 Jul. 15, 2010

Related U.S. Application Data

(60) Provisional application No. 61/145,003, filed on Jan. 15, 2009.

(51) Int. Cl.
*A61N 1/372* (2006.01)
*A61N 1/36* (2006.01)

(52) U.S. Cl.
CPC ........ *A61N 1/37247* (2013.01); *A61N 1/37241* (2013.01); *A61N 1/37282* (2013.01); *A61N 1/36075* (2013.01)

(58) Field of Classification Search
CPC ..... A61N 1/36; A61N 1/36075; A61N 1/372; A61N 1/37241; A61N 1/37247
USPC ..................................................... 607/59, 60
See application file for complete search history.

(56) References Cited

U.S. PATENT DOCUMENTS

| 2,123,980 | A | 7/1938 | Warwick |
| 2,182,071 | A | 12/1939 | Crossley |
| 3,357,434 | A | 12/1967 | Abell |
| 3,746,004 | A | 7/1973 | Jankelson |
| 3,859,103 | A | 1/1975 | Yoshiyagawa et al. |
| 3,862,321 | A | 1/1975 | Adams et al. |
| 3,914,283 | A | 10/1975 | Okamoto et al. |

(Continued)

FOREIGN PATENT DOCUMENTS

| EP | 69427 A2 | 1/1983 |
| EP | 0970813 A2 | 1/2000 |

(Continued)

OTHER PUBLICATIONS

Iliff et al.; Epoxyeicosanoids as mediators of neurogenic vasodilation in cerebral vessels; Am J Physiol Heart Circ Physiol; vol. 296; pp. 1352-1363; Mar. 20, 2009.

(Continued)

*Primary Examiner* — Christopher A Flory
(74) *Attorney, Agent, or Firm* — Shay Glenn LLP

(57) ABSTRACT

Methods and apparatus for delivering therapy from an implanted neurostimulator to a patient are provided. One feature is an external controller that acts as a gateway for therapy. The external controller can be a handheld controller that communicates wirelessly with the implanted neurostimulator. In some embodiments, the controller communicates with a database to determine a therapy approval status of the neurostimulator. Therapy can be approved by a physician prescription, or by prepayment, for example. In some embodiments, the neurostimulator is deactivated when no approved therapies remain.

20 Claims, 3 Drawing Sheets

(56) References Cited

U.S. PATENT DOCUMENTS

| | | |
|---|---|---|
| 3,923,060 A | 12/1975 | Ellinwood, Jr. |
| 3,925,469 A | 12/1975 | Adams et al. |
| 4,073,917 A | 2/1978 | Sandberg et al. |
| 4,102,344 A | 7/1978 | Conway et al. |
| 4,117,160 A | 9/1978 | Molnar et al. |
| 4,147,804 A | 4/1979 | Diamond et al. |
| 4,217,349 A | 8/1980 | Katsube et al. |
| 4,298,603 A | 11/1981 | Chang et al. |
| 4,305,402 A | 12/1981 | Katims |
| 4,352,820 A | 10/1982 | Scurlock et al. |
| 4,379,161 A | 4/1983 | Thominet et al. |
| 4,397,845 A | 8/1983 | Allen |
| 4,441,210 A | 4/1984 | Hochmair et al. |
| 4,495,174 A | 1/1985 | Allcock et al. |
| 4,519,400 A | 5/1985 | Brenman et al. |
| 4,529,601 A | 7/1985 | Broberg et al. |
| 4,550,733 A | 11/1985 | Liss et al. |
| 4,551,453 A | 11/1985 | Marsili |
| 4,565,200 A | 1/1986 | Cosman |
| 4,592,359 A | 6/1986 | Galbraith |
| 4,622,219 A | 11/1986 | Haynes |
| 4,627,438 A | 12/1986 | Liss et al. |
| 4,632,940 A | 12/1986 | Chiarino et al. |
| 4,646,744 A | 3/1987 | Capel |
| 4,692,147 A | 9/1987 | Duggan |
| 4,695,576 A | 9/1987 | af Ekenstam et al. |
| 4,718,423 A | 1/1988 | Willis et al. |
| 4,727,145 A | 2/1988 | Press |
| 4,776,349 A | 10/1988 | Nashef et al. |
| 4,784,142 A | 11/1988 | Liss et al. |
| 4,830,008 A | 5/1989 | Meer |
| 4,833,149 A | 5/1989 | Press |
| 4,856,526 A | 8/1989 | Liss et al. |
| 4,870,086 A | 9/1989 | Sandberg |
| 4,871,475 A | 10/1989 | Lubowitz et al. |
| 4,886,493 A | 12/1989 | Yee |
| 4,920,979 A | 5/1990 | Bullara |
| 4,937,078 A | 6/1990 | Mezei et al. |
| 4,976,711 A | 12/1990 | Parins et al. |
| 5,038,781 A | 8/1991 | Lynch |
| 5,085,868 A | 2/1992 | Mattsson et al. |
| 5,178,156 A | 1/1993 | Takishima et al. |
| 5,193,539 A | 3/1993 | Schulman et al. |
| 5,199,428 A | 4/1993 | Obel et al. |
| 5,215,086 A | 6/1993 | Terry, Jr. et al. |
| 5,227,165 A | 7/1993 | Domb et al. |
| 5,234,957 A | 8/1993 | Mantelle |
| 5,255,691 A | 10/1993 | Otten |
| 5,259,387 A | 11/1993 | dePinto |
| 5,314,458 A | 5/1994 | Najafi et al. |
| 5,318,592 A | 6/1994 | Schaldach |
| 5,330,515 A | 7/1994 | Rutecki et al. |
| 5,335,657 A | 8/1994 | Terry, Jr. et al. |
| 5,344,438 A | 9/1994 | Testerman et al. |
| 5,360,805 A | 11/1994 | Ask et al. |
| 5,387,587 A | 2/1995 | Hausler et al. |
| 5,411,546 A | 5/1995 | Bowald et al. |
| 5,420,151 A | 5/1995 | Hammarberg et al. |
| 5,428,006 A | 6/1995 | Bechgaard et al. |
| 5,433,739 A | 7/1995 | Sluijter et al. |
| 5,458,626 A | 10/1995 | Krause |
| 5,458,631 A | 10/1995 | Xavier |
| 5,490,520 A | 2/1996 | Schaefer et al. |
| 5,514,131 A | 5/1996 | Edwards et al. |
| 5,540,730 A | 7/1996 | Terry, Jr. et al. |
| 5,540,734 A | 7/1996 | Zabara |
| 5,545,219 A | 8/1996 | Kuzma |
| 5,558,622 A | 9/1996 | Greenberg |
| 5,560,351 A | 10/1996 | Gravenstein et al. |
| 5,569,166 A | 10/1996 | Stone |
| 5,578,061 A | 11/1996 | Stroetmann et al. |
| 5,591,216 A | 1/1997 | Testerman et al. |
| 5,640,764 A | 6/1997 | Strojnik |
| 5,645,570 A | 7/1997 | Corbucci |
| 5,653,734 A | 8/1997 | Alt |
| 5,658,318 A | 8/1997 | Stroetmann et al. |
| 5,660,837 A | 8/1997 | Lundquist |
| 5,676,955 A | 10/1997 | Ansmann et al. |
| 5,690,692 A | 11/1997 | Fleming |
| 5,700,282 A | 12/1997 | Zabara |
| 5,707,400 A | 1/1998 | Terry, Jr. et al. |
| 5,711,316 A | 1/1998 | Elsberry et al. |
| 5,713,922 A | 2/1998 | King |
| 5,735,817 A | 4/1998 | Shantha |
| 5,756,520 A | 5/1998 | Ask et al. |
| 5,766,605 A | 6/1998 | Sanders et al. |
| 5,824,027 A | 10/1998 | Hoffer et al. |
| 5,843,021 A | 12/1998 | Edwards et al. |
| 5,861,014 A | 1/1999 | Familoni |
| 5,865,843 A | 2/1999 | Baudino |
| 5,938,688 A | 8/1999 | Schiff |
| 6,001,088 A | 12/1999 | Roberts et al. |
| 6,006,134 A | 12/1999 | Hill et al. |
| 6,016,449 A | 1/2000 | Fischell et al. |
| 6,026,326 A | 2/2000 | Bardy |
| 6,058,331 A | 5/2000 | King |
| 6,073,048 A | 6/2000 | Kieval et al. |
| 6,093,145 A | 7/2000 | Vom Berg et al. |
| 6,094,598 A | 7/2000 | Elsberry et al. |
| 6,104,957 A | 8/2000 | Alo et al. |
| 6,128,538 A | 10/2000 | Fischell et al. |
| 6,132,384 A | 10/2000 | Christopherson et al. |
| 6,134,474 A | 10/2000 | Fischell et al. |
| 6,141,590 A | 10/2000 | Renirie et al. |
| 6,146,380 A | 11/2000 | Racz et al. |
| 6,161,044 A | 12/2000 | Silverstone |
| 6,161,048 A | 12/2000 | Sluijter et al. |
| 6,178,349 B1 | 1/2001 | Kieval |
| 6,205,359 B1 | 3/2001 | Boveja |
| 6,246,912 B1 | 6/2001 | Sluijter et al. |
| 6,251,126 B1 | 6/2001 | Ottenhoff et al. |
| 6,259,952 B1 | 7/2001 | Sluijter et al. |
| 6,262,377 B1 | 7/2001 | Nielsen et al. |
| 6,269,270 B1 | 7/2001 | Boveja |
| 6,292,695 B1 | 9/2001 | Webster, Jr. et al. |
| 6,308,105 B1 | 10/2001 | Duysens et al. |
| 6,353,792 B1 | 3/2002 | Murthy |
| 6,356,786 B1 | 3/2002 | Rezai et al. |
| 6,356,787 B1 | 3/2002 | Rezai et al. |
| 6,356,788 B2 | 3/2002 | Boveja |
| 6,366,814 B1 | 4/2002 | Boveja et al. |
| 6,400,982 B2 | 6/2002 | Sweeney et al. |
| 6,405,079 B1 | 6/2002 | Ansarinia |
| 6,432,986 B2 | 8/2002 | Levin |
| 6,438,423 B1 | 8/2002 | Rezai et al. |
| 6,456,786 B1 | 9/2002 | Uchida et al. |
| 6,458,157 B1 | 10/2002 | Suaning |
| 6,491,940 B1 | 12/2002 | Levin |
| 6,511,500 B1 | 1/2003 | Rahme |
| 6,526,318 B1 | 2/2003 | Ansarinia |
| 6,564,096 B2 | 5/2003 | Mest |
| 6,564,102 B1 | 5/2003 | Boveja |
| 6,610,713 B2 | 8/2003 | Tracey |
| 6,615,081 B1 | 9/2003 | Boveja |
| 6,633,779 B1 | 10/2003 | Schuler |
| 6,647,296 B2 | 11/2003 | Fischell et al. |
| 6,665,562 B2 | 12/2003 | Gluckman et al. |
| 6,668,191 B1 | 12/2003 | Boveja |
| 6,735,475 B1 | 5/2004 | Whitehurst et al. |
| 6,760,626 B1 | 7/2004 | Boveja |
| 6,788,975 B1 | 9/2004 | Whitehurst et al. |
| RE38,654 E | 11/2004 | Hill et al. |
| 6,819,956 B2 | 11/2004 | DiLorenzo |
| 6,832,114 B1 | 12/2004 | Whitehurst et al. |
| 6,853,858 B2 | 2/2005 | Shalev |
| 6,885,888 B2 | 4/2005 | Rezai |
| 6,978,180 B2 | 12/2005 | Tadlock |
| 7,003,352 B1 | 2/2006 | Whitehurst |
| 7,027,860 B2 | 4/2006 | Bruninga et al. |
| 7,047,078 B2 | 5/2006 | Boggs, II et al. |
| 7,076,307 B2 | 7/2006 | Boveja et al. |
| 7,113,033 B2 | 9/2006 | Barnett |
| 7,117,033 B2 | 10/2006 | Shalev et al. |
| 7,120,489 B2 | 10/2006 | Shalev et al. |

(56) References Cited

U.S. PATENT DOCUMENTS

| | | |
|---|---|---|
| 7,149,574 B2 | 12/2006 | Yun et al. |
| 7,167,751 B1 | 1/2007 | Whitehurst et al. |
| 7,191,012 B2 | 3/2007 | Boveja et al. |
| 7,203,548 B2 | 4/2007 | Whitehurst et al. |
| 7,209,787 B2 | 4/2007 | DiLorenzo |
| 7,277,758 B2 | 10/2007 | DiLorenzo |
| 7,285,118 B1 | 10/2007 | Lozano |
| 7,286,879 B2 | 10/2007 | Wallace |
| 7,292,890 B2 | 11/2007 | Whitehurst et al. |
| 7,340,298 B1 | 3/2008 | Barbut |
| 7,349,743 B2 | 3/2008 | Tadlock |
| 7,363,076 B2 | 4/2008 | Yun et al. |
| 7,369,897 B2 | 5/2008 | Boveja et al. |
| 7,403,821 B2 | 7/2008 | Haugland et al. |
| 7,477,945 B2 | 1/2009 | Rezai et al. |
| 7,494,458 B2 | 2/2009 | Fischell et al. |
| 7,532,938 B2 | 5/2009 | Machado et al. |
| 7,561,919 B2 | 7/2009 | Shalev et al. |
| 7,623,924 B2 | 11/2009 | Narciso, Jr. |
| 7,640,057 B2 | 12/2009 | Libbus et al. |
| 7,689,276 B2 | 3/2010 | Dobak |
| 7,763,034 B2 | 7/2010 | Siegel et al. |
| 7,848,816 B1 | 12/2010 | Wenzel et al. |
| 8,055,347 B2* | 11/2011 | Lamensdorf et al. ............ 607/45 |
| 8,195,297 B2 | 6/2012 | Penner |
| 8,489,192 B1 | 7/2013 | Hlavka et al. |
| 8,583,229 B2 | 11/2013 | Rezai et al. |
| 8,781,574 B2 | 7/2014 | Pless et al. |
| 8,886,325 B2 | 11/2014 | Boling et al. |
| 2002/0026222 A1 | 2/2002 | Schauerte et al. |
| 2002/0073334 A1* | 6/2002 | Sherman et al. .............. 713/201 |
| 2002/0107553 A1 | 8/2002 | Hill et al. |
| 2002/0169365 A1 | 11/2002 | Nakada et al. |
| 2003/0004549 A1 | 1/2003 | Hill et al. |
| 2003/0018367 A1 | 1/2003 | DiLorenzo |
| 2003/0018368 A1* | 1/2003 | Ansarinia ...................... 607/46 |
| 2003/0028147 A1 | 2/2003 | Aves et al. |
| 2003/0060857 A1 | 3/2003 | Perrson et al. |
| 2003/0065374 A1 | 4/2003 | Honeck |
| 2003/0100924 A1 | 5/2003 | Foreman et al. |
| 2003/0133877 A1 | 7/2003 | Levin |
| 2003/0144709 A1 | 7/2003 | Zabara et al. |
| 2003/0176898 A1* | 9/2003 | Gross et al. .................... 607/54 |
| 2003/0181951 A1 | 9/2003 | Cates |
| 2003/0181958 A1 | 9/2003 | Dobak, III |
| 2003/0181959 A1 | 9/2003 | Dobak, III |
| 2003/0212440 A1 | 11/2003 | Boveja |
| 2003/0216792 A1 | 11/2003 | Levin et al. |
| 2004/0015204 A1 | 1/2004 | Whitehurst et al. |
| 2004/0019364 A1 | 1/2004 | Kieval et al. |
| 2004/0049235 A1 | 3/2004 | Deno et al. |
| 2004/0093053 A1 | 5/2004 | Gerber et al. |
| 2004/0172084 A1 | 9/2004 | Knudson et al. |
| 2004/0210295 A1 | 10/2004 | Brushey |
| 2004/0230255 A1 | 11/2004 | Dobak, III |
| 2004/0236381 A1 | 11/2004 | Dinsmoor et al. |
| 2005/0038484 A1 | 2/2005 | Knudson et al. |
| 2005/0065562 A1 | 3/2005 | Rezai |
| 2005/0065573 A1 | 3/2005 | Rezai |
| 2005/0075701 A1 | 4/2005 | Shafer |
| 2005/0075702 A1 | 4/2005 | Shafer |
| 2005/0102006 A1 | 5/2005 | Whitehurst et al. |
| 2005/0143378 A1 | 6/2005 | Yun et al. |
| 2005/0143626 A1 | 6/2005 | Prescott |
| 2005/0143787 A1 | 6/2005 | Boveja et al. |
| 2005/0149156 A1 | 7/2005 | Libbus et al. |
| 2005/0153885 A1* | 7/2005 | Yun et al. ..................... 514/12 |
| 2005/0154419 A1 | 7/2005 | Whitehurst et al. |
| 2005/0154426 A1 | 7/2005 | Boveja et al. |
| 2005/0159790 A1 | 7/2005 | Shalev |
| 2005/0197675 A1 | 9/2005 | David et al. |
| 2005/0209654 A1 | 9/2005 | Boveja et al. |
| 2005/0216070 A1 | 9/2005 | Boveja et al. |
| 2005/0234523 A1 | 10/2005 | Levin et al. |
| 2005/0281751 A1 | 12/2005 | Levin |
| 2006/0004423 A1 | 1/2006 | Boveja et al. |
| 2006/0020299 A1 | 1/2006 | Shalev |
| 2006/0064140 A1 | 3/2006 | Whitehurst et al. |
| 2006/0074450 A1 | 4/2006 | Boveja et al. |
| 2006/0074463 A1* | 4/2006 | Seeberger et al. .............. 607/60 |
| 2006/0079945 A1 | 4/2006 | Libbus |
| 2006/0085046 A1 | 4/2006 | Rezai |
| 2006/0095088 A1 | 5/2006 | De Ridder |
| 2006/0100667 A1 | 5/2006 | Machado et al. |
| 2006/0100668 A1 | 5/2006 | Ben-David et al. |
| 2006/0100671 A1 | 5/2006 | Ridder |
| 2006/0106285 A1 | 5/2006 | Boulais et al. |
| 2006/0111754 A1 | 5/2006 | Rezai |
| 2006/0116721 A1 | 6/2006 | Yun et al. |
| 2006/0122660 A1 | 6/2006 | Boveja et al. |
| 2006/0149337 A1 | 7/2006 | John |
| 2006/0167497 A1 | 7/2006 | Armstrong et al. |
| 2006/0173495 A1 | 8/2006 | Armstrong et al. |
| 2006/0178666 A1 | 8/2006 | Cosman et al. |
| 2006/0184211 A1 | 8/2006 | Gaunt et al. |
| 2006/0195169 A1 | 8/2006 | Gross |
| 2006/0206165 A1 | 9/2006 | Jaax et al. |
| 2006/0235484 A1 | 10/2006 | Jaax et al. |
| 2006/0287678 A1* | 12/2006 | Shafer ............... 607/2 |
| 2006/0293723 A1 | 12/2006 | Whitehurst et al. |
| 2007/0021801 A1 | 1/2007 | Heruth et al. |
| 2007/0021802 A1 | 1/2007 | Heruth et al. |
| 2007/0027483 A1 | 2/2007 | Maschino et al. |
| 2007/0027484 A1 | 2/2007 | Guzman et al. |
| 2007/0027486 A1 | 2/2007 | Armstrong |
| 2007/0027498 A1 | 2/2007 | Maschino et al. |
| 2007/0039625 A1 | 2/2007 | Heruth et al. |
| 2007/0049988 A1 | 3/2007 | Carbunaru et al. |
| 2007/0066997 A1 | 3/2007 | He et al. |
| 2007/0067004 A1 | 3/2007 | Boveja et al. |
| 2007/0083245 A1 | 4/2007 | Lamensdorf et al. |
| 2007/0100411 A1 | 5/2007 | Bonde |
| 2007/0106143 A1 | 5/2007 | Flaherty |
| 2007/0112404 A1 | 5/2007 | Mann et al. |
| 2007/0156177 A1 | 7/2007 | Harel et al. |
| 2007/0156179 A1 | 7/2007 | S.E. |
| 2007/0167984 A1 | 7/2007 | Kieval et al. |
| 2007/0203521 A1 | 8/2007 | Dobak et al. |
| 2007/0233193 A1 | 10/2007 | Craig |
| 2007/0250119 A1* | 10/2007 | Tyler et al. .................. 607/2 |
| 2007/0250145 A1 | 10/2007 | Kraus et al. |
| 2007/0255368 A1 | 11/2007 | Bonde et al. |
| 2007/0255369 A1 | 11/2007 | Bonde et al. |
| 2007/0293906 A1 | 12/2007 | Cowan et al. |
| 2008/0027346 A1 | 1/2008 | Litt et al. |
| 2008/0033509 A1 | 2/2008 | Shalev et al. |
| 2008/0046053 A1 | 2/2008 | Wagner et al. |
| 2008/0071318 A1 | 3/2008 | Brooke et al. |
| 2008/0086182 A1 | 4/2008 | Ben-David et al. |
| 2008/0103547 A1 | 5/2008 | Okun et al. |
| 2008/0103569 A1 | 5/2008 | Gerber |
| 2008/0132933 A1 | 6/2008 | Gerber |
| 2008/0132981 A1 | 6/2008 | Gerber |
| 2008/0132982 A1 | 6/2008 | Gerber |
| 2008/0140000 A1 | 6/2008 | Shuros et al. |
| 2008/0161877 A1 | 7/2008 | Kirby et al. |
| 2008/0161894 A1 | 7/2008 | Ben-David et al. |
| 2008/0172102 A1* | 7/2008 | Shalev ............... 607/45 |
| 2008/0183237 A1 | 7/2008 | Errico et al. |
| 2008/0183246 A1 | 7/2008 | Patel et al. |
| 2008/0183253 A1 | 7/2008 | Bly |
| 2008/0262566 A1 | 10/2008 | Jaax |
| 2008/0269716 A1 | 10/2008 | Bonde et al. |
| 2009/0012577 A1 | 1/2009 | Rezai et al. |
| 2009/0036949 A1 | 2/2009 | Kokones et al. |
| 2009/0105783 A1 | 4/2009 | Solberg et al. |
| 2009/0118780 A1 | 5/2009 | DiLorenzo |
| 2009/0216287 A1 | 8/2009 | Ansarinia |
| 2009/0254147 A1 | 10/2009 | Ansarinia |
| 2009/0264956 A1 | 10/2009 | Rise et al. |
| 2009/0276005 A1 | 11/2009 | Pless |
| 2009/0276025 A1 | 11/2009 | Burnes et al. |
| 2009/0312817 A1 | 12/2009 | Hogle et al. |
| 2009/0320845 A1* | 12/2009 | Fishman et al. ......... 128/204.23 |

(56) References Cited

U.S. PATENT DOCUMENTS

| | | |
|---|---|---|
| 2010/0185258 A1 | 7/2010 | Papay |
| 2010/0228316 A1 | 9/2010 | Errico et al. |
| 2010/0228318 A1 | 9/2010 | Errico et al. |
| 2010/0268306 A1 | 10/2010 | Maniak et al. |
| 2011/0029037 A1 | 2/2011 | Rezai et al. |
| 2011/0046432 A1 | 2/2011 | Simon et al. |
| 2012/0209286 A1 | 8/2012 | Papay et al. |
| 2012/0270876 A1 | 10/2012 | Yun et al. |
| 2013/0110195 A1 | 5/2013 | Fletcher et al. |
| 2013/0116745 A1 | 5/2013 | Fletcher et al. |
| 2013/0131636 A1 | 5/2013 | Rezai et al. |
| 2013/0178829 A1 | 7/2013 | Rezai et al. |
| 2014/0207220 A1 | 7/2014 | Boling et al. |
| 2014/0303436 A1 | 10/2014 | Pless et al. |
| 2015/0196753 A1 | 7/2015 | Levin |

FOREIGN PATENT DOCUMENTS

| | | |
|---|---|---|
| EP | 754060 B1 | 3/2003 |
| RU | 2108817 C1 | 4/1996 |
| WO | WO85/00599 A1 | 2/1985 |
| WO | WO92/07605 A1 | 5/1992 |
| WO | WO95/21821 A1 | 2/1994 |
| WO | WO97/02000 A1 | 1/1997 |
| WO | WO97/15548 A1 | 5/1997 |
| WO | WO97/23467 A1 | 7/1997 |
| WO | WO97/38675 A1 | 10/1997 |
| WO | WO01/85094 A2 | 11/2001 |
| WO | WO01/97905 A1 | 12/2001 |
| WO | WO03/082123 A2 | 10/2003 |
| WO | WO2005/105202 A1 | 11/2005 |

OTHER PUBLICATIONS

Narouze et al.; Sphenopalatine ganglion radiofrequency ablation for the management of chronic cluster headache; Headache; vol. 49; pp. 571-577; Apr. 2009.

Gromova et al.; Sinusoidal modulated currents in comprehensive treatment of children with bronchial asthma; Voprosy Kurortologii Fizioterapii, I Lechebnoi Fizicheskoi Kultury; May-Jun.; (3); pp. 45-47; 1981 (w/ English Abstract).

Karashurov et al.; Radio frequency electrostimulation of the gangliated cord of the sympathetic nerve in patients with bronchial asthma; Surgery (Khigurgiia); vol. 1; pp. 44-46; 2000 (w/ English Abstract).

Rao et al., "Effectiveness of temporal pattern in the input to a ganglion: Inhibition in the cardiac ganglion of spiny lobsters", J of Neurobiology, vol. 1, No. 2, pp. 233-245 (1969) (abstract).

Sinkj et al., "Electroneurography", Encyclopedia of Medical Devices and Instrumentation, Second Edition: pp. 109-132 (2006).

Boling et al.; U.S. Appl. No. 12/765,712 entitled "Implantable Neurostimulator with Integral Hermetic Electronic Enclosure, Circuit Substrate, Monolithic Feed-Through, Lead Assembly and Anchoring Mechanism," filed Apr. 22, 2010.

Wingeier et al.; U.S. Appl. No. 12/791,690 entitled "Methods and Devices for Adrenal Stimulation," filed Jun. 1, 2010.

Guo et al.; Treatment of primary trigeminal neuralgia with acupuncture at the sphenopalatine ganglion; Journal of traditional chinese medicine; vol. 15(1) pp. 31-33; 1995.

Karavis, "The neurophysiology of acupuncture: a viewpoint", Acupuncture in Medicine, vol. 15(1): 33-42 (May 1997).

Alstadhaug, K.B.; Migraine and the hypothalamus; Cephalalgia (Blackwell Publishing Ltd.); pp. 1-9; 2009.

Ardell et al.; "Differential sympathetic regulation of automatic, conductile, and contractile tissue in dog heart;" American Physiological Society; pp. H1050-H1059; Jun. 6, 1988.

Babe, "Treatment of sphenopalatine ganglion neuralgia", An Otorrinolaringol Ibero Am, vol. 16(5): 463-74 (1989) (abstract).

Barre, "Cocaine as an abortive agent in cluster headache", Headache, vol. 22: 69-73 (1982).

Benumof et al.; Pulmonary artery catheterization; In Clinical Procedures in Anesthesia and Intensive Care; JB Lippincott Company; pp. 405-441; 1992.

Berger et al., "Does topical anesthesia of the sphenopalatine ganglion with cocaine or lidocaine relieve low back pain?", Anesth Analg, vol. 35: 87-108 (1925).

Boysen et al.; Parasympathetic tonic dilatory influences on cerebral vessels; Autonomic Neuroscience: Basic and Clinical; vol. 147; pp. 101-104; 2009.

Brooksby et al.; Dynamic changes in splanchnic blood flow and blood volume in dogs during activation of sympathetic nerves; Circulation Research; vol. 29; pp. 227-238; 1971.

Brooksby et al; Release of blood from the splanchnic circulation in dogs; Circulation Research; vol. 31; pp. 105-118; 1972.

Browne et al., "Concurrent cervical and craniofacial pain" Oral Surg Oral Med Oral Path 86(6): 633-640 (Dec. 1998).

Carneiro et al.; Blood reservoir function of dog spleen, liver and intestine; American Journal of Physiology; vol. 232; No. 1; pp. H67-H72; 1977.

Carroll et al., "Motor cortex stimulation for chronic neuropathic pain: a preliminary study of 10 cases" Pain 84:431-437 (2000).

Cepero et al., "Long-term results of sphenopalatine ganglioneurectomy for facial pain", Am J Otolaryngol, 8(3): 171-4 (1987).

Cheatham et al.; Shock: An overview, surgical critical care service; Department of Surgical Education; Orlando Regional Medical Center; 5th ed.; pp. 1-40; 2003.

Cohen et al.; Sphenopalatine ganglion block for postdural puncture headache; Anaesthesia; vol. 64; pp. 574-575; 2009.

Cook, "Cryosurgery of headache", Res Clin Stud Headache, vol. 5: 86-101 (1978) (abstract).

Cooper et al.; Neural effects on sinus rate and atrioventricular conduction produced by electrical stimulation from a transvenous electrode catheter in the canine right pulmonary artery; Circulation Research; vol. 46; pp. 48-57; 1980.

Cutrer et al., "Effects of PNU-109,291, a selective 5H-T1D receptor agonist, on electrically induced dural plasma extravasation and capsaicin-evoked c-fos immunoreactivity within trigeminal nucleus caudalis" Neuropharm 38:1043-1053 (1999).

Delepine et al., "Plasma protein extravasation induced in the rat dura mater by stimulation of the parasympathetic sphenopalatine ganglion", Exp Neurology, vol. 147: 389-400 (1997).

Devoghel, "Cluster headache and sphenopalatine block", Acta Anaesthesio Belg, vol. 32(1), pp. 101-107 (1981).

Feindel et al., "The tentorial nerves and localization of intracranial pain in man" Neurology 555-563 (1955).

Ferrante et al., "Sphenopalatine ganglion block for the treatment of myofascial pain of the head, neck, and shoulders", Reg Anesth Pain, vol. 23(1): 30-6 (1988) (abstract).

Frisardi et al., "Electric versus magnetic transcranial stimulation of the trigeminal system in healthy subjects. Clinical applications in gnathology.", J Oral Rehabil, 24(12): 920-8 (1986) (abstract).

Goadsby et al., "Differential effects of low dose CP122,288 and eletriptan on Fos expression due to stimulation of the superior sagittal sinus in cat" Pain 82:15-22 (1999).

Goadsby et al., "Stimulation of an intracranial trigeminally-innervated structure selectively increases cerebral blood flow" Brain Research 751:247-252 (1997).

Goadsby et al., "Substance P blockade with the potent and centrally acting antagonist GR205171 does not effect central trigeminal activity with superior sagittal sinus stimuation" Neuroscience 86(1):337-343 (1998).

Goadsby et al., "The trigeminovascular system and migraine: studies characterizing cerebrovascular and neuropeptide changes seen in humans and cats" Ann Neurol 33:48-56 (1993).

Goadsby et al., Effect of stimulation of trigeminal ganglion on regional cerebral blood flow in cats; Am J. Physiol.; vol. 22; pp. R270-R274; 1987.

Goadsby, "Sphenopalatine ganglion stimulation increases regional blood flow independent of glucose utilization in the cat", Brain Research, vol. 506: 145-8 (1990).

Gregoire, "Cluster headaches", Can Nurse, vol. 87(9): 33-5 (1991) (abstract).

Hardebo, Jan-Erik; Activation of pain fibers to the internal carotid artery intracranially may cause the pain and local signs of reduced

(56) References Cited

OTHER PUBLICATIONS sympathetic and enhanced parasympathetic activity in cluster headache; Headache; 31; pp. 314-320; May 1991.
Hardebo, Jan-Erik; On pain mechanisms in cluster headache; Headache; 31; pp. 91-106; 1991.
Headache Classification Committee of the International Headache Society, "Classification and diagnostic criteria for headache disorders, cranial neuralgias and facial pain", Cephalalgia, Supp & 0:13, 19-24 and 35-38 (1988).
Heusch et al.; Adrenergic mechanisms in myocardial ischemia; Supp. to Basic Research in Cardiology; vol. 85; 1990.
Hillier; Monitored anesthesia care; Clinical Anesthesia; Ch. 47; pp. 1239-1254; 2001.
Hoskin et al., "Fos expression in the trigeminocervical complex of the cat after stimulation of superior sagittal sinus is reduced by L-NAME" Neuroscience Letters 266:173-176 (1999).
Hudson; Basic principles of clinical pharmacology; Clinical Anesthesia; Ch. 11; pp. 239-260; 2001.
Ibarra, Eduardo; Neuromodulacion del Ganglio Esfenopalation para Aliviar los Sintomas del la Cefalea en Raciomos; Boletin El Dolor; vol. 46, No. 16; pp. 12-18; 2007 (with English translation).
Janes et al.; Anatomy of human extrinsic cardiac nerves and ganglia; American Journal of Cardiology; vol. 57; pp. 299-309; 1986.
Janzen et al., "Sphenopalatine blocks in the treatment of pain in fibromyalgia and myofascial pain syndrome", Laryngoscope, vol. 107(10): 1420-2 (1997).
Kittrelle et al., "Cluster headache. Local anesthetic abortive agents", Arch Neurol, vol. 42(5): 496-8 (May 1985).
Kosaras et al.; Sensory innervation of the calvarial bones of the mouse; The Journal of Comparative Neurology (John Wiley & Sons); 48 pgs.; 2009.
Kudrow et al., "Rapid and sustained relief of migraine attacks with intranasal lidocaine: preliminary findings", Headache, vol. 25: 79-82 (1995).
Kudrow, "Natural history of cluster headaches—part 1 outcome of drop-out patients", Headache, vol. 22: 203-6 (1982).
Kushiku et al.; Upregulation of Immunoreactive Angiotensin II Release and Angiotensinogen mRNA Expression by High-Frequency Preganglionic Stimulation at the Canine Cardiac Sympathetic Ganglia; Circ Res.; 88; pp. 110-116; 2001.
Lambert et al.; Comparative effects of stimulation of the trigeminal ganglion and the superior sagittal sinus on cerebral blood flow and evoked potentials in the cat; Brain Research; vol. 453; pp. 143-149; 1988.
Lebovits et al., "Sphenopalatine ganglion block: clinical use in the pain management clinic", Clin J Pain, vol. 6(2): 131-6 (1990).
Levine et al.; Central venous and pulmonary artery catheter monitoring; Critical Care Monitoring from Pre-Hospital to the ICU; pp. 145-158.
Maizels et al., "Intranasal lidocaine for treatment of migraine", JAMA, vol. 276 (4): 319-21 (1996).
Manahan et al., "Sphenopalatine ganglion block relieves symptoms of trigeminal neuralgia: a case report", Nebr Med J, vol. 81(9): 306-9 (1996) (abstract).
Matsumoto et al.; Effective sites by sympathetic beta-andrenergic and vagal nonadrenergic inhibitory stimulation in constricted airways; Am Rev Respir Dis; vol. 132; pp. 1113-1117; Nov. 1985.
Matthey et al.; Bedside catheterization of the pulmonary artery: risks compared with benefits; In Clinical Procedures in Anesthesia and Intensive Care; JB Lippincott Company; vol. 109; pp. 826-834; 1988.
Meyer et al., "Sphenopalatine ganglionectomy for cluster headache", Arch Otolaryngol, vol. 92(5): 475-84 (Nov. 1970).
Meyerson et al.; Alleviation of Atypical trigeminal pain by stimulation of the gasserian ganglion via an implanted electrode; Acta Neurochirurgica; supp. 30; pp. 303-309; 1980.
Moskowitz et al., "Basic mechanisms in vascular headache" Headache 8 (4):801-815 (Nov. 1990).
Moskowitz, Michael; Cluster headache: evidence for a pathophysiologic focus in the superior pericarotid cavernous sinus plexus; Headache; vol. 28; pp. 584-586; 1988.

Murphy et al.; Human cardiac nerve stimulation; The Annals of Thoracic Surgery; vol. 54; p. 502; 1992.
Narouze et al.; Sphenopalatine ganglion stimulation for the acute treatment of intractable migraine; American Academy of Pain Medicine Annual Meeting Abstracts; pp. 226 (Abstract No. 157); 2009.
Nguyen et al., "Chronic motor cortex stimulation in the treatment of central and neuropathic pain. Correlations between clinical, electrophysiological and anatomical data" Pain 82:245-251 (1999).
Onofrio et al., "Surgical treatment of chronic cluster headache", Mayo Clin Proc, vol. 61(7), pp. 537-544 (1986).
Peterson et al., "Sphenopalatine ganglion block: a safe and easy method for the management of orofacial pain", Cranio, vol. 13(3): 177-81 (1995) (abstract).
Phebus et al., "The non-peptide NK-1 receptor antagonist LY303870 inhibits neurogenic dural inflammation in guinea pigs" Life Sciences 60(18):1553-1561 (1997).
Pollock et al., "Stereotactic radiosurgical treatment of sphenopalatine neuralgia", J Neurosurg, vol. 87(3): 450-3 (1997).
Reder et al., "Sphenopalatine ganglion block in treatment of acute and chronic pain", Diagnosis and treatment of chronic pain, John Wright, publisher, 97-108 (1982).
Reuter et al.; Experimental models of migraine; Funct Neurol; suppl. 15; pp. 9-18; 2000.
Ruskin, "Contributions to the study of the sphenopalatine ganglion", Laryngoscope, vol. 35(2): 87-108 (1925).
Ruskin; Sphenopalatine (nasal) gaglion: remote effects including "psychosomatic" symptons, rage reaction, pain, and spasm; Arch Phys Med Rehabil; vol. 60; pp. 353-359; Aug. 1979.
Ryan et al., "Sphenopalatine ganglion neuralgia and cluster headache: comparisons, contrasts, and treatment", Headache, vol. 17: 7-8 (1977).
Saade et al., "Patient-administered sphenopalatine ganglion block", Reg Anesth, vol. 21(1): 68-70 (1996) (abstract).
Sanders et al., "Efficacy of sphenopalatine ganglion blockade in 66 patients suffering from cluster headache: a 12- to 70- month follow-up evaluation", J Neurosurg., vol. 87(6), pp. 876-880 (Dec. 1997).
Scherlag et al.; Endovascular stimulation within the left pulmonary artery to induce slowing of heart rate and paroxysmal atrial fibrillation; Cardiovascular Research; vol.54; pp. 470-475; 2002.
Schulz et al., "Localization of epileptic auras induced on stimulation by subdural electrodes" Epilepsia 38(12) 1321-1329 (1997).
Scott et al.; Trigger point injections for chronic non-malignant musculoskeletal pain: a systematic review; Pain Medicine; vol. 10; No. 1; pp. 54-69; 2009.
Seylaz et al., "Effect of stimulation of the sphenopalatine ganglion on cortical blood flow in the rat", J Cerebr Blood Flow and Metab, vol. 8: 875-8 (1988).
Shuster et al., "Treatment of vasomotor rhinitis, trigeminal neuralgia and Sluder's syndrome by irradiation of the sphenopalatine ganglion with helium-neon lasers", Vestin Otorinolaringol, vol. 4: 35-40 (1988).
Sluder, "The syndrome of sphenopalatine ganglion neuralgia", Am J Medicament Sci, vol. 111: 868-878 (1910).
Sluder; The anatomical and clinical relations of the sphenopalatine (Meckel's) ganglion to the nose and its accessory sinuses; NY Med. J.; vol. 90; pp. 293-298; Aug. 1909.
Steude; Percutaneous electro stimulation of the trigeminal nerve in patients with atypical trigeminal neuralgia; Neurochirurgia; vol. 21; pp. 66-69; 1978.
Storer et al., "Microiontophoretic application of serotonin (5HT) 1B/1D agonists inhibits trigeminal cell firing in the cat" Brain 120:2171-2177 (1997).
Strassman et al., "Sensitization of meningeal sensory neurons and the origin of headaches" Nature 384:560-563 (Dec. 1996).
Suzuki at al., "Selective electrical stimulation of postganglionic cerebrovascular parasympathetic nerve fibers originating from the sphenopalatine ganglion enhances cortical blood flow in the rat", J Cerebr Blood Flow and Metab, vol. 10: 383-391 (1990).
Suzuki et al.; Trigeminal fibre collaterals storing substance P and calcitonin gene-related peptide ; Neuroscience; vol. 30; No. 3; pp. 595-604; 1989.

(56) References Cited

OTHER PUBLICATIONS

Taub et al., "Chronic electrical stimulation of the gasserian ganglion for the relief of pain in a series of 34 patients", J Neurosurg, vol. 86: 197-202 (1997).

Thalamic Stimulation and Trigeminal Neuralgia; Neuroscience Pathways (Publication of The Cleveland Clinic Foundation); Spring 1998 newsletter; pp. 1-2.

Toda et al.; Cerebral blood flow regulation by nitric oxide: recent advances; Pharmacol Rev; vol. 61; No. 1; pp. 62-97; 2009.

Vitek; Mechanisms of deep brain stimulation: excitation or inhibition; Movement Disorders; vol. 17; supp. 3; pp. S69-S72; 2002.

Walters et al.; Cerebrovascular projections from the sphenopalatine and otic ganglia to the middle cerebral artery of the cat; Stroke; vol. 17; pp. 488-494; 1986.

Young, "Electrical stimulation of the trigeminal nerve root for the treatment of chronic facial pain", J Neurosurg, vol. 83: 72-78 (1995).

Zarembinski et al.; Sphenopalatine ganglion block in traumatic trigeminal neuralgia and the outcome to radiosurgical ablation; American Academy of Pain Medicine Annual Meeting Abstracts; pp. 200 (abstract No. 102); 2009.

Witte et al.; Experimental heart failure in rats: effects on cardiovascular circadian rhythms and on myocardial ?-adrenergic signaling; Cardiovasc Res; vol. 47; pp. 350-358; 2000.

Yee et al.; Circadian variation in the effects of aldosterone blockade on heart rate variability and QT dispersion in congestive heart failure; J. Am. Coll. Cardiol.; vol. 37; pp. 1800-1807; 2001.

Pless et al.; U.S. Appl. No. 12/649,119 entitled "Integrated Delivery and Visualization Tool for a Neuromodulation System," filed Dec. 29, 2009.

Levin, Bruce; U.S. Appl. No. 12/683,301 entitled "Method for Directed Intranasal Administration of a Composition," filed Jan. 6, 2010.

Wingeier et al.; U.S. Appl. No. 12/692,444 entitled "Method and Devices for Adrenal Stimulation," filed Jan. 22, 2010.

Moskowitz; Neurogenic inflammation in the pathophysiology and treatment of migraine; Neurology; vol. 43; suppl. 3; pp. S16-S20; 1993.

Cooke-Ariel; Circadian variations in cardiovascular function and their relation to the occurrence and timing of cardiac events; Am. J. Heath. Syst. Pharm.; vol. 55; supp. 3; pp. S5-S11; Nov. 15, 1998.

Giles; Importance of long-acting andiotensin-converting enzyme inhibitors for congestive heart failure; Am. J. Cardiol.; vol. 70; pp. 98C-101C; Oct. 8, 1992.

Grossmann; Effects of cardiac glycosides on 24-h ambulatory blood pressure in healthy volunteers and patients with heart failure; Eur J Clin Invest; vol. 31; Iss.S2; pp. 26-30; Apr. 2001.

Gudovsky et al.; Surgical treatment of bronchial asthma; Surgery (Khigurgiia); vol. 7; pp. 14-18; Jul. 2002.

Karashurov et al.; Evolution of surgical treatment of bronchial asthma; Surgery (Khigurgiia); vol. 11; pp. 57-60; Nov. 1999.

Kim et al.; Sympathectomy: Open and Thoracoscopic; In: Surgical Management of Pain; Thieme Medical Publishers, Inc.; RD 595.5. 587; Chapter 55; Jan. 2002.

Mansoor et al.; Ambulatory blood pressure monitoring: technique and application in the study of cardiac dysfunction and congestive heart failure; Congest Heart Fail; vol. 7; pp. 319-324; Nov./Dec. 2001.

Panina et al.; Assessment of autonomic tone over a 24-hour period in patients with congestive heart failure: relation between mean heart rate and measures of heart rate variability; Am. H. J.; vol. 129; pp. 748-753; Apr. 1995.

Teerlink et al.; Hemodynamic variability and circadian rhythm in rats with heart failure: role of locomotor activity; Am. J. Physiol.; vol. 264; pp. H2111-2118; Jun. 1993.

Theodosopoulos et al.; Endoscopic approach to the infratemporal fossa: anatomic study; Neurosurgery; vol. 66; No. 1; pp. 196-203; Jan. 2010.

Van Horne et al.; Multichannel semiconductor-based electrodes for in vivo electrochemical and electrophysiological studies in rat CNS; Neuroscience Letters; vol. 120; pp. 249-252; Nov. 1990.

Fletcher et al.; U.S. Appl. No. 14/849,351 entitled "Approval per use implanted neurostimulator," filed Sep. 9, 2015.

Boling et al.; U.S. Appl. No. 14/858,904 entitled "Implantable neurostimulator with integral hermetic electronic enclosure, circuit substrate, monolithic feed-through, lead assembly and achoring mechanism," filed Sep. 18, 2015.

Vollmer et al.; Adrenal medullary catecholamine secretion patterns in rats evoked by reflex and direct neural stimulation; Clinical and Experimental Hypertension; V22(7&8); pp. 705-715; Oct.-Nov. 2000.

* cited by examiner

APPROVAL PER USE IMPLANTED NEUROSTIMULATOR

CROSS REFERENCE TO RELATED APPLICATIONS

This application claims the benefit under 35 U.S.C. 119 of U.S. Provisional Patent Application No. 61/145,003, filed Jan. 15, 2009, titled "PAY PER DOSE IMPLANTED NEUROSTIMULATOR." This application is herein incorporated by reference in its entirety.

INCORPORATION BY REFERENCE

All publications, including patents and patent applications, mentioned in this specification are herein incorporated by reference in their entirety to the same extent as if each individual publication was specifically and individually indicated to be incorporated by reference.

FIELD OF THE INVENTION

This invention is directed to an active implantable device that has features that facilitate the metered prescription of use over time, which is particularly relevant for devices that can dispense a large amount or otherwise unlimited amount of therapy without external intervention. The invention may be applied to a range of implantable medical devices including without limitation implantable drug pumps, functional electrical neurostimulators, such as spinal cord stimulators, stimulators for incontinence and deep brain stimulators. This disclosure will focus on an implantable neurostimulator used to treat headache.

BACKGROUND OF THE INVENTION

There are implantable medical devices that are loaded with or are otherwise able to administer or deliver a large or unlimited amount of therapy. For example, an implanted drug pump could contain many years worth of drug, or an inductively powered, rechargeable, or primary cell implantable stimulator could deliver therapy in perpetuity as governed by the external controller, charger or battery life. These types of implanted devices present benefits to the patient and the healthcare system in that the often invasive implantation procedures are limited. However, they pose some unique clinical risks in that the patient carries with them, either within the implant or by virtue of the implant, a much larger quantity or amount of therapy than would otherwise be prescribed by a physician, an insurer or a manufacturer.

An implanted neurostimulator used to treat headaches can be used very frequently for the rest of the patient's lifetime. Given the unlimited nature of therapy delivered in this manner, the patient could choose to activate the neurostimulator when it is not needed. Without some limitation mechanism, the medical device may become much like an over-the-counter pharmaceutical where usage is entirely up to the user.

The inability to limit use of such medical devices poses potential clinical risks to the patient, such as over-use (if over use is a clinical problem) that leads to ineffective therapy over time at therapy levels that were once effective. The absence of usage limits may also fatigue the internal components of the device, resulting in a shorter therapeutic lifetime. Further, it can pose increased financial burden to the healthcare system due to poorer clinical outcomes or more frequent device failures. Finally, it can also present financial constraints on patients, for example if the device is priced based on all potential uses of the device, or constraints on an insurer or the manufacturer if patients use the device much more than intended.

SUMMARY OF THE INVENTION

A method of delivering therapy to a patient comprises checking a therapy approval status of an implanted neurostimulator on a database through an external controller, and delivering therapy from the implanted neurostimulator to the patient if the therapy approval status of the implanted neurostimulator is approved.

In some embodiments, therapy is not delivered from the implanted neurostimulator to the patient if the therapy approval status of the implanted neurostimulator is not approved. In one embodiment, the therapy approval status of the implanted neurostimulator may not be approved if the database indicates that the implanted neurostimulator is deactivated. In other embodiments, the status of the implanted neurostimulator may not be approved if the database indicates payment is past due.

In some embodiments, the database is stored at a location separate from the external controller.

In one embodiment, the implanted neurostimulator is implanted on or near a sphenopalatine ganglion of the patient.

In some embodiments, the external controller is an external handheld controller.

In one embodiment, a list of deactivated and not approved neurostimulators on the external controller after the checking step.

A method of approving therapy in a patient is provided, comprising implanting a medical device in the patient, approving a set number of therapies to be delivered from the medical device to the patient, and deactivating the medical device when no approved therapies remain.

In some embodiments, the approving step further comprises approving a set number of therapies to be delivered from the medical device to the patient with a physician prescription. In other embodiments, the approving step further comprises approving a set number of therapies to be delivered from the medical device to the patient with payment by the patient.

The method can further comprise checking a therapy approval status of the medical device with a handheld controller. In some embodiments, the method further comprises directing the medical device to deliver therapy to the patient with the handheld controller.

In one embodiment, the method can further comprise re-activating the medical device by approving an additional number of therapies to be delivered from the medical device to the patient.

In another embodiment, the method can further comprise storing a therapy approval status of the medical device on a database. In one embodiment, the method can further comprise accessing the database with a handheld controller to determine the therapy approval status of the medical device.

In some embodiments, the medical device is a neurostimulator.

A system for delivering therapy to a patient is also provided, comprising an implantable neurostimulator configured to deliver therapy to the patient, a database containing a therapy approval status of the implantable neurostimulator, and an external controller in communication with the database and the implantable neurostimulator, the external controller configured to direct the implantable neurostimulator to deliver therapy to the patient if the therapy approval status of the implantable neurostimulator is approved.

In some embodiments, the implantable neurostimulator is sized and configured to be implanted on or near a sphenopalatine ganglion.

In one embodiment, the external controller is a handheld controller.

In some embodiments, the external controller is configured to update and store a list of the therapy approval status of the implantable neurostimulator. In other embodiments, the external controller is in wireless communication with the implantable neurostimulator and the database.

In some embodiments, the therapy is electrical stimulation.

In other embodiments, the external controller is configured to deactivate the implantable stimulator if the therapy approval status of the implantable neurostimulator is not approved.

In some embodiments, the database is stored remotely from the implantable neurostimulator and the external controller.

DETAILED DESCRIPTION OF THE INVENTION

Figure 1:
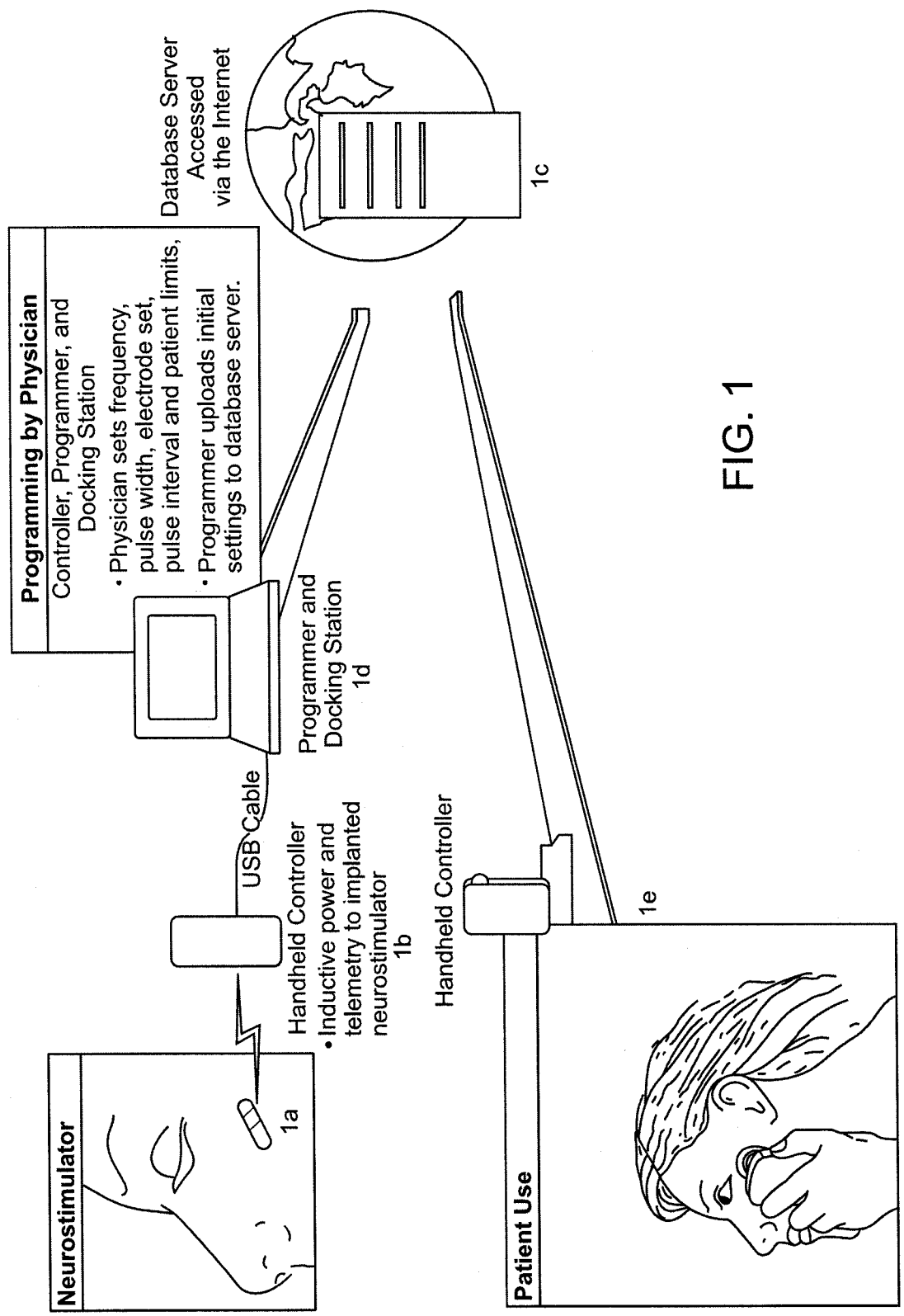
FIG. 1 shows a high level view of the neurostimulation system.

Referring to FIG. 1, a stimulator 1a comprises an implantable millimeter-scale, biocompatible, hermetic electronics enclosure and integral stimulation lead system. Further details of a suitable stimulator are described in U.S. Provisional Application No. 61/171,749 titled, "IMPLANTABLE ELECTRICAL NERVE STIMULATOR WITH INTEGRAL HERMETIC ELECTRONIC ENCLOSURE, CIRCUIT SUBSTRATE, AND MONOLYTHIC FEED-THROUGH," filed on Apr. 22, 2009. The stimulator can be an inductively powered system having stored programmed stimulation parameters and bi-directional telemetry to facilitate communication between the implanted neurostimulator and an external controller. The electronics enclosure can include an ASIC, various passive components, and a secondary coil for radio frequency transfer of power and communication. The integral lead system provides an electrical connection between the electronics housed in the hermetic enclosure and one or more stimulating electrodes at the distal end of the lead. Each of the one or more electrodes provides a site for electrical stimulation of the target anatomy.

The controller 1b can be a handheld external, rechargeable, ergonomic, energy delivery device that transfers energy to the implanted stimulator with near field electromagnetic induction. The controller can also be a communication system transferring information such as stimulation parameters to the implanted stimulator with bi-directional telemetry. The controller can receive commands from an external programmer 1d, such as though a USB connection, for example. The controller can communicate with the implanted stimulator once it's within close proximity to the stimulator. In one embodiment the controller has features that allow it to deliver power along with sending commands to and receiving data from the neurostimulator.

In one embodiment, the controller 1b communicates with the programmer 1d through a USB cable connected between the controller and the programmer. When connected to the programmer, the controller goes into a "pass through" mode in which all or some of its controls are disabled and it simply serves as a communication bridge between the PC and the stimulator.

In an alternate embodiment, the controller communicates with the programmer wirelessly using WIFI, Blue Tooth, infrared or similar technology.

The controller can include a power source such as batteries, a coil to inductively power the implant and send/receive data, a microcontroller, firmware, wireless broadband card, supporting circuitry, an ergonomically shaped housing and various manual control features such as a therapy level adjustment knob or buttons, an off/on switch, and a display.

In one embodiment, a proprietary handshaking protocol occurs between the stimulator and the controller to ensure that only authorized devices can power up and communicate with the stimulator. The handshaking communication protocol ensures that only authorized devices can cause the stimulator to deliver therapy. This protects the system from situations where a user is attempting to bypass the approval system with a controller manufactured by a third party.

The protocol could be implemented in a number of different ways including a system where the stimulator contains a coded key that is sent to the controller on power up. The key is then encrypted by the controller and sent back to the stimulator. The stimulator decrypts the key and verifies that it matches the value originally sent. If the values do not match the stimulator would deny therapy. To make breaking into the system more difficult, the stimulator could require that a certain amount of time expire before it would resend and decrypt the key again. This would help defend against "brute force" attacks where a device pretending to be a controller could send repeated versions of the key at a very rapid rate until by chance the proper value unlocks the stimulator. Any number of other handshaking security protocols could be used with the goal being that unauthorized $3^{rd}$ party controllers are denied access to the stimulator.

The Programmer 1d can be a PC based system used by physicians to configure stimulators that have been previously implanted in patients. It can interface with the controller 1b wirelessly or through a USB connection to the controller. The Programmer can then instruct the controller to communicate with and receive data from the implant. The programmer can be used to associate patient and physician information with the serial number of the stimulator. In addition, it can also be used to program therapy settings into the stimulator. These therapy parameters include, but are not limited to, electrode configuration, stimulation amplitude, duration, and frequency. All information entered by the physician including stimulation parameters and stimulator serial number can be transferred to a central database 1c via a wireless interne connection on completion of the stimulator programming session. Transmission of session data can be done either via the controller or the programmer wirelessly.

Figure 2:
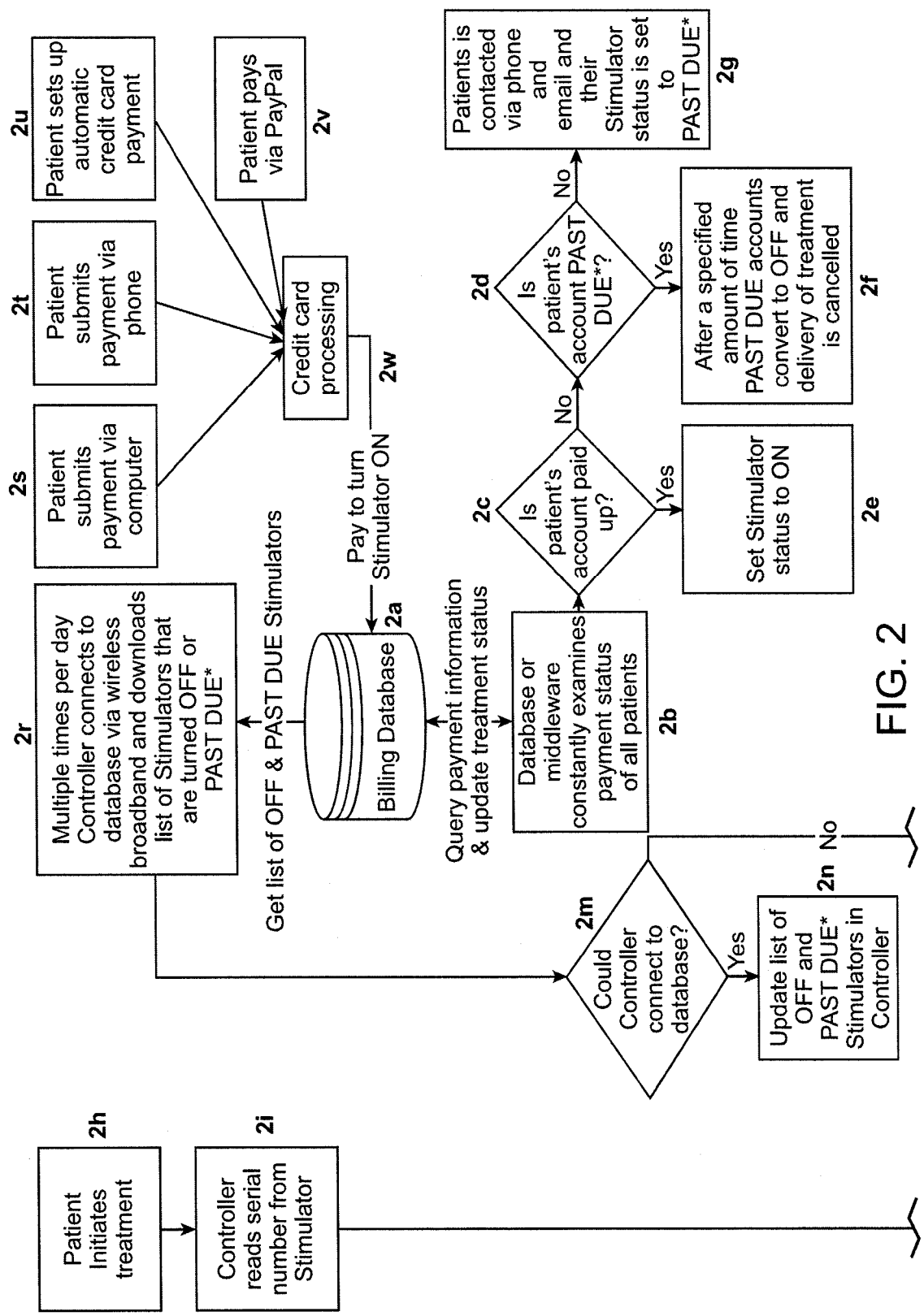
FIG. 2 shows an embodiment of the approval per use system.
Figure 2:
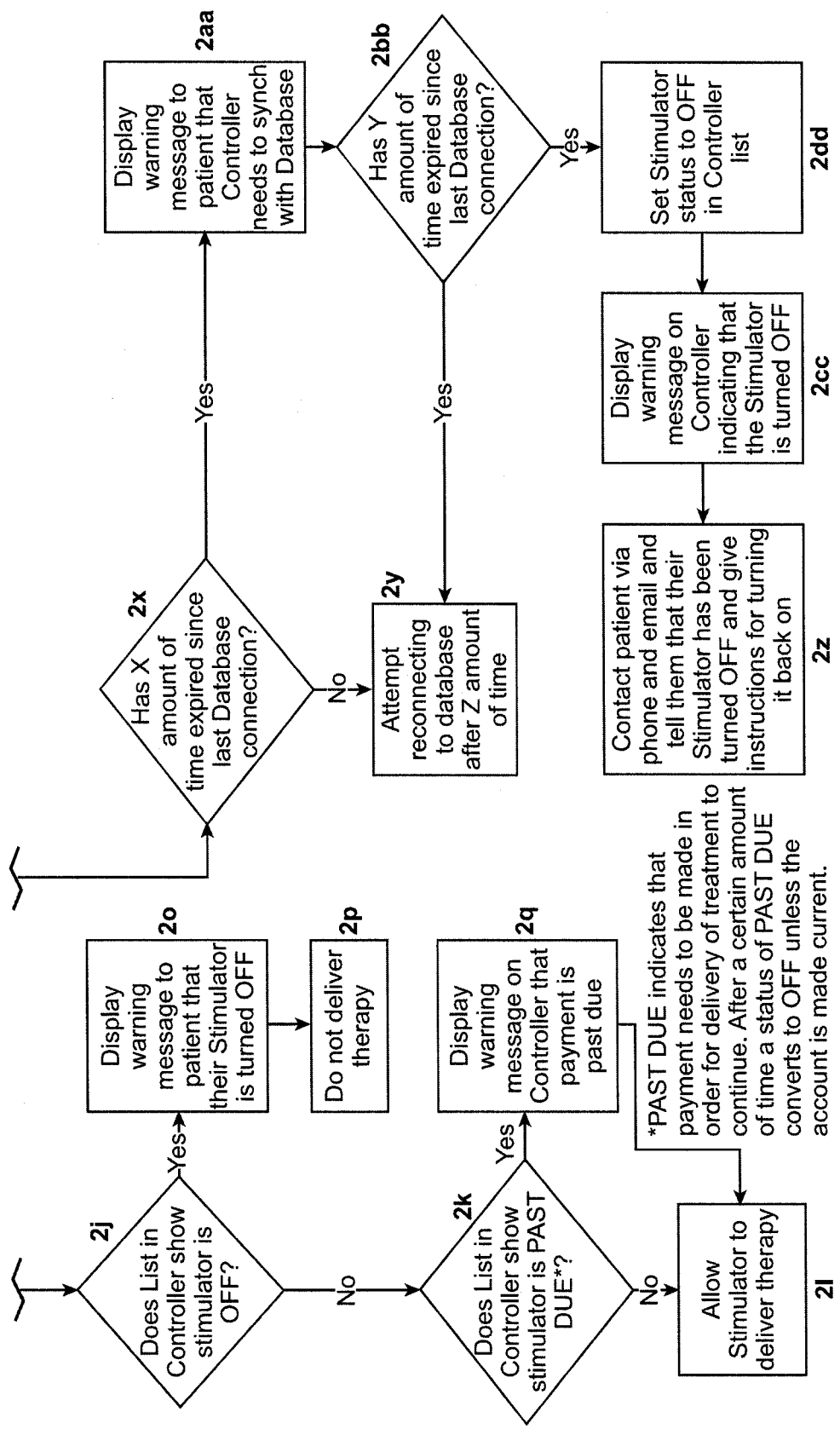

In the flowchart diagram shown in FIG. 2, the patient can be approved for a certain number of uses of the handheld controller to apply therapy. This is analogous to being prescribed and paying for an ingestible drug on a specific dose regimen. Uses of the handheld controller, and hence therapy, are managed by comparing patient therapy usage, activation of the implanted neurostimulator via the handheld controller, in the database with the number of approved uses for the patient. The approval can be any set of criteria or combinations thereof, for example but without limitation; clinical, like a physician's prescription, or; financial, like pre-paid uses or an automatic payment system from stored credit card information.

For the system to work, information from the database is used to allow activation of the patient's neurostimulator, via the controller, if approved uses are available. If no more approvals are available, messages can be posted to the display of the controller. The neurostimulator can be "turned off" or deactivated if no more approvals are intended for that patient. This can be done by wirelessly communicating with all controllers the serial numbers of implanted neurostimulators that are "OFF" or are "NOT APPROVED".

In FIG. 2, the database shown in step 2a is the central repository for information relating to approval status. The database may be any technology that stores information and allows that information to be read and updated. In one embodiment, this database can be an industry standard such as Oracle, Microsoft SQL Server, etc. and would allow standard SQL (Structured Query Language) commands to be executed against it. The database can comprise a table or tables that contain the serial numbers of all neurostimulators that have been implanted in patients. The database can also contain the approval status of these patients. For example, if there are no remaining physician-prescribed uses, or if the patient is delinquent in payment then the patient approval status can be set to "NOT APPROVED." The database can also contain billing information like credit card or bank account information, patient contact information for use in sending out notices and bills, and whether the associated stimulator should be turned ON, OFF, or if the account is NOT APPROVED.

Middleware software, shown in steps 2b through 2g, is the software that may run between the database and external applications such as the controller software or payment processing service, and would provide a process to read data from and write data to the database, along with logic to analyze the database and update its information accordingly.

For example, referring to steps 2b through 2g, at step 2b the database or middleware can examine the payment status of all patients. This can be done by request, by schedule, or done in real-time, for example. At step 2c, the database or middleware examines if the patients account is paid in full. If the account is paid up, then the stimulator status can be set to ON at step 2e. If the account is not paid in full, then the database or middleware can examine if the patient's account is PAST DUE at step 2d. If the patient's account is PAST due, then at step 2f the stimulator status of PAST DUE accounts convert to OFF after a specified amount of time, delivery of therapy from the stimulator is canceled, and the patients are notified of their account status.

In an alternate embodiment, the database is configured such that connections could be made directly to it and it would have the capability of updating itself when new information is available. For example, if the database lists a certain stimulator as being OFF and an approval is received, for example due to a physician's prescription or a patient payment, the database or the middleware can update the field in the database to indicate that the stimulator is now ON.

The middleware can be either a web based or a client based application, where the client based application can be software that runs on the controller or applications associated with payment or prescription processing. Middleware may also be used to generate reports used to monitor patient trends or to improve the overall system.

Upon being powered up, the stimulator's ability to deliver treatment is determined by the controller which checks the stimulator's serial number against its list of OFF and NOT APPROVED stimulators. The stimulator, as described above, is "unaware" of its own of approval status and whether it should be enabled or disabled. This means that each time the stimulator is powered up by any controller it can deliver therapy if allowed by the controller regardless of approval status.

A method of approving the use of an implanted neurostimulator, and hence therapy, will now be described. Referring to steps 2h through 2l and 2o through 2q, at step 2h the patient can initiate therapy by using the handheld controller to attempt to activate the neurostimulator. At step 2i, the controller can read the serial number from the stimulator. At step 2j, the serial number is checked against the database or middleware to determine if the stimulator status is OFF. If the status is OFF, then a warning message can be displayed to the patient at step 2o and the stimulator does not deliver therapy at step 2p. The message can inform the patient that approval is needed, such as by physician prescription or patient payment. Alternatively, if the stimulator status is not OFF, then the database or middleware is checked to see if the stimulator status is PAST DUE. If the status is PAST DUE, then a warning message can be displayed to the patient at step 2q and the stimulator is allowed to deliver therapy at step 2l. If the status is not PAST DUE, then the stimulator is also allowed to deliver therapy at step 2l.

The controller, as described above, is the gateway for stimulation. The controller maintains a list of OFF/deactivated and NOT APPROVED stimulators and uses this list to determine if the stimulators it communicates with should be allowed to deliver therapy (see steps 2h through 2l and 2o through 2q, as described above).

The controller's list is updated from the database via a wireless broadband transceiver built into the controller. Referring to step 2r, the controller connects to the database (e.g. connects multiple times per day) and downloads a list of stimulators that are turned OFF or are PAST DUE. If the controller successfully connects to the database at step 2m, then the list is updated on the controller at step 2n.

If the controller is unable to update its list of stimulators from the database for an extended period of time, a warning message is displayed to the patient indicating that they must synchronize with the database or their stimulator will be disabled (see steps 2m, 2x, 2aa). After this period of time expires, subsequent attempts by the patient to initiate therapy will be denied and a warning message will be displayed on the controller indicating that the stimulator is disabled (see steps 2m, 2x, 2aa, 2bb, 2dd, 2cc, 2z). Therapy will not be delivered to this stimulator until approval is granted and an updated list indicating that the stimulator can be enabled is downloaded from the database to the controller. This function guards against situations where the patient either intentionally or inadvertently is outside of broadband range and the controller cannot verify approval. If a certain amount of time has not expired since the last database connection, the stimulator will attempt to reconnect to the database after a predetermined time in step 2y.

If the patient does not live in an area that supports broadband access that would allow them to receive approvals the patient may be granted approvals using a special numeric access key that the physician or provider enters into the controller to provide a limited number of immediate therapies. This number could also be provided to the patient via email, conventional mail, text message, website, phone, in person, or other means of communication. Another way of granting approval that would provide instantaneous therapy is a hardware dongle that plugs into the controller and unlocks it while the dongle is plugged in. In an alternate implementation plugging in the dongle could load a predetermined number of approvals into the controller. The dongle could then be removed and the patient could receive therapy.

Alternate embodiments of this design include but are not limited to: Instead of downloading a list of OFF stimulators the controller might submit a direct query for information relating to the Stimulators that it specifically works with. For example if the controller works with Stimulators with serial number 11111 and 22222 it would only query the database for the status of these devices rather than the status of all stimulators that are OFF. If therapy is initiated with a stimulator the controller has not interfaced with, the controller would first attempt to look up the status of this stimulator in the database and if the database connection was successful the controller would treat the stimulator accordingly. If the connection was not successful a warning message would be displayed and treatment would be delivered but subsequent treatments would be disabled until the stimulator status can be successfully downloaded from the database.

In another embodiment, instead of using a list of OFF stimulators to determine which stimulators can deliver therapy the patient could receive a set number of approvals for a fee. In this method the controller would query the number of treatments remaining for a particular stimulator from the database and would deduct from this number each time treatment is delivered. This would require that the controller not only download the number of available treatments from the database but that it also have the ability to upload the number of treatments used to ensure proper tracking of the number of approvals remaining. This would also facilitate a system where the number of therapies available to the patient is shown as a number on the display of their controller.

Yet another embodiment could be a system where controllers would come preset with a certain number of treatments at a set fee and when those treatments have been used up the patient would return the controller and either have it "refilled" or instead they might exchange their controller for another that is loaded with the number of treatments that are approved by the physician. Reimbursement for this could come through an insurance company, directly from the patient, or through another reimbursement source such as Medicare/Medicaid.

Approvals for use can be generated from physician's prescriptions, analogous to being prescribed a pharmaceutical, or from patient payment analogous to a cellular phone pay-per-use billing system, or a combination thereof. Patient approvals may also be generated instantaneously in acute or emergency situations by approved providers, such as physicians or other medical personal.

Approvals generated by physician prescription can be communicated to the Database in a number of different ways including but not limited to web-based direct programming either by existing electronic prescription systems or by a custom website or program associated with the Database, by phone using an automated system or by manual input of the approval, or automatically recurring approvals at certain time intervals analogous to refills on prescription pharmaceuticals.

Approvals granted acutely in an emergency situation can be made as described above for physician prescriptions. Approvals may also be granted by a special numeric access key that the physician or provider enters into the controller to provide a limited number of immediate therapies. Another means of granting approval that would provide instantaneous therapy is a hardware dongle that plugs into the controller and unlocks it while the dongle is plugged in. In an alternate implementation plugging in the dongle could load a predetermined number of approvals into the controller. The dongle could then be removed and the patient could receive therapy.

Approvals generated by payment can be made in a number of different ways including but not limited to credit card payments made over the web (see step $2s$), credit card payments made over the phone (see step $2t$), automated credit card payments (see step $2u$), payments made from a payment vendor such as Paypal (see step $2v$), and payments made directly from a bank account either automatically or manually. The system is configured to accept any form of electronic payment.

Once approval is granted, the information for that patient is updated in the database and if the account is made current the database is updated to indicate that the patient's neurostimulator can be turned ON (see steps $2w$, $2e$, & $2a$ through $2c$) and is removed from the controller list of OFF or NOT APPROVED neurostimulators. If the prescription or the amount of payment is insufficient to bring the account current, then the database is updated to indicate that the neurostimulator should be turned OFF (see steps $2d$, $2f$, $2g$).

Prescription based approvals can take any number of forms, for example but without limitation, total number of uses, or time-dependent rate of uses like number of uses per day, per month or per year, or uses that expire in a defined amount of time. Total number of uses would be analogous to getting a prescription for one container of drugs, and would require further physician interaction to get more drugs prescribed. Time-dependent rate of use approval would be analogous to being prescribed a certain number of pills to be used over a certain amount of time, and after said time had elapsed the pills could be refilled.

There are types of physician prescription approval schemes for which no pharmaceutical analogy exists too. For example, in the case of a neurostimulator to treat headache, it may be undesirable to activate the device too frequently as described previously.

Other approval options may include but are not limited to pharmacist approval for a limited number of doses and immediate physician approval in an office, emergency room, or patient room setting.

In the case of pharmacist approval a patient may have forgotten to contact their physician or other provider to renew their prescription or perhaps their physician is out of town. As with prescription medications a pharmacist may at their discretion provide a limited number of doses to the patient.

In the hospital setting a physician may want to intervene immediately and provide approval to address an acute episode or to provide prophylactic therapy prior to a procedure.

For payment based approvals, a number of different billing strategies can be utilized. A prepaid treatment based strategy where the patient would pay in advance for a certain number of treatments and this number would be decremented each time the patient used the system to deliver therapy.

A second plan is similar to the billing system used for a cellular phone service. This plan would charge each patient a monthly fee whether they use the system for treatment or not. If the number of treatments included in the monthly fee is exceeded, then an additional fee is charged. This situation is similar to when a cellular customer exceeds the number of minutes in their monthly plan.

A third option would be if the patient pays a large one time fee for "Product Lifetime Service." This would allow their stimulator to be used for the lifetime of the product without further billing. A fourth option would be a variable plan where the patient can choose to pay by the day, the month, the year, or multiple years. Any number of other plans would work as well with the primary goal being that payment is made either on the basis of the number of times therapy is delivered or by a recurring fee that is charged regardless of whether therapies are delivered.

It is also possible that the entity being billed for services is an institution rather than the individual patient. In this scenario the patient could be removed from the billing loop and their insurance carrier, government health care provider, or other health care provider could be billed directly. Examples of government health care providers include but are not limited to federal organizations such as Medicare, Veterans Administration, state-sponsored programs such as Medi-Cal, and programs sponsored by counties, local governments or federal governments.

If the patient is being billed directly and it is determined that their account is past due, a number of actions can be taken to notify the patient that their stimulator is about to be turned OFF. These actions might include, but are not limited to, sending emails, contact via phone, instant messages, physical letters sent via US mail, and notices sent to their controller (see step 2g). If a certain amount of time has expired and the patient has not made the necessary payment, the database is updated to reflect that their stimulator should be turned OFF (see step 2f) and their serial number will be added to the list of disabled serial numbers downloaded by each controller from the database.

If an entity, like and insurance carrier, is being billed there could be two tiers of notification: The first being that the provider is notified by the means described in the prior paragraph or by representatives from the device manufacturer; and the second being that if the entity has failed to provide payment the patient is notified that they need to take action to keep their account current.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A method of approving therapy in a patient, comprising:
    implanting a medical device in the patient;
    approving a set number of approved therapies to be delivered from the medical device to the patient; and
    deactivating the medical device when no approved therapies remain.

2. The method of claim 1 wherein the approving step further comprises approving a set number of therapies to be delivered from the medical device to the patient with a physician prescription.

3. The method of claim 1 wherein the approving step further comprises approving a set number of therapies to be delivered from the medical device to the patient with payment by the patient.

4. The method of claim 1 further comprising checking a therapy approval status of the medical device with a handheld controller.

5. The method of claim 4 further comprising directing the medical device to deliver therapy to the patient with the handheld controller.

6. The method of claim 1 further comprising re-activating the medical device by approving an additional number of therapies to be delivered from the medical device to the patient.

7. The method of claim 1 further comprising storing a therapy approval status of the medical device on a database.

8. The method of claim 7 further comprising accessing the database with a handheld controller to determine the therapy approval status of the medical device.

9. The method of claim 1 wherein the medical device is a neurostimulator.

10. The system of claim 1 wherein the set number of approved therapies comprises a pre-determined number of approved therapies.

11. A system for delivering therapy to a patient, comprising:
    an implantable neurostimulator configured to deliver therapy to the patient;
    a database containing a count of approved therapies of the implantable neurostimulator; and
    an external controller in communication with the database and the implantable neurostimulator, the external controller configured to direct the implantable neurostimulator to deliver therapy to the patient if approved therapies remain.

12. The system of claim 11 wherein the implantable neurostimulator is sized and configured to be implanted on or near a sphenopalatine ganglion.

13. The system of claim 11 wherein the external controller is a handheld controller.

14. The system of claim 11 wherein the external controller is configured to update and store a list of the count of remaining approved therapies of the implantable neurostimulator.

15. The system of claim 11 wherein the external controller is in wireless communication with the implantable neurostimulator and the database.

16. The system of claim 11 wherein the therapy is electrical stimulation.

17. The system of claim 11 wherein the external controller is configured to deactivate the implantable stimulator if no approved therapies remain.

18. The system of claim 11 wherein the database is stored remotely from the implantable neurostimulator and the external controller.

19. The system of claim 11 wherein the controller is configured to direct the database to deduct an approved therapy from the count of approved therapies when therapy is delivered to the patient.

20. A method of delivering therapy to a patient, comprising:
    implanting a neurostimulator in the patient;
    checking on a database a count of approved therapies of the neurostimulator;
    if the count of approved therapies is greater than zero, delivering therapy from the implanted neurostimulator to the patient; and
    deducting an approved therapy from the count of approved therapies on the database.

* * * * *